United States Patent [19]

Abblard et al.

[11] 4,382,928
[45] May 10, 1983

[54] FUNGICIDAL COMPOSITIONS

[75] Inventors: Jean Abblard, St. Didier au Mt. D'Or; Jean-Michel Gaulliard, Orlienas; Guy Lacroix, Lyons, all of France

[73] Assignee: Rhone-Poulenc Agrochimie, France

[21] Appl. No.: 131,400

[22] Filed: Mar. 18, 1980

Related U.S. Application Data

[63] Continuation-in-part of Ser. No. 17,945, Mar. 6, 1979, abandoned.

[30] Foreign Application Priority Data

Mar. 16, 1978 [FR] France .............................. 78 08237

[51] Int. Cl.³ ............................................ A01N 57/00
[52] U.S. Cl. .................................... 424/211; 260/944; 424/128
[58] Field of Search ................. 424/199, 211; 260/944

[56] References Cited

U.S. PATENT DOCUMENTS

| 4,119,724 | 10/1978 | Thizy et al. ............................ 424/45 |
| 4,139,616 | 2/1979 | Ducret et al. ......................... 424/222 |
| 4,188,381 | 2/1980 | Ducret et al. ......................... 424/199 |

OTHER PUBLICATIONS

Chemical Abstracts 71:70062m (1969).
Chemical Abstracts 55:12292h (1961).

Primary Examiner—Leonard Schenkman
Attorney, Agent, or Firm—Robert E. Burns; Emmanuel J. Lobato; Bruce L. Adams

[57] ABSTRACT

A composition for combatting fungal and bacterial diseases in plants is disclosed which contains, as the active ingredient, a compound of the formula:

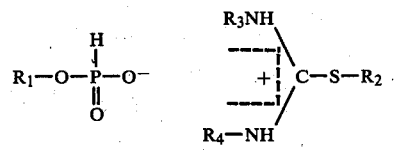

in which: $R_1$ is hydrogen or an alkyl radical containing from 1 to 6 carbon atoms, $R_2$ is an alkyl radical containing from 1 to 18 carbon atoms, $R_1$ and $R_2$ can additionally form an ethylene or propylene chain which is optionally substituted by alkyls containing from 1 to 3 carbon atoms, and $R_3$ and $R_4$, which are identical or different, are hydrogen, an alkyl radical containing from 1 to 18 carbon atoms, a cycloalkyl radical containing from 3 to 7 carbon atoms, an alkenyl radical containing from 3 to 18 carbon atoms, the phenyl radical or the benzyl radical, in association with an inert carrier which is acceptable in agriculture.

17 Claims, No Drawings

FUNGICIDAL COMPOSITIONS

CROSS-REFERENCE TO RELATED APPLICATIONS

The present application is a continuation-in-part of our copending application Ser. No. 17,945, filed Mar. 6, 1979 and now abandoned.

BACKGROUND OF THE INVENTION

The present invention relates to new fungicidal compositions which are intended for combatting fungal diseases in plants and contain isothiouronium phosphites as the active ingredient. The invention also comprises a process for protecting plants against fungal diseases, using these compositions.

Fungicidal compositions which are intended for combatting fungal diseases in plants and contain organic salts of phosphorous acid or of 0-alkylphosphorous acid as the active ingredient are known from French applications 2,252,056 and 2,254,276. Although these compounds possess valuable fungicidal properties, especially against vine mildew, they exhibit the disadvantage of being phytotoxic, which prohibits any practical use.

SUMMARY OF THE INVENTION

The aim of the present invention is to provide new fungicidal compositions which are based on organic phosphites and do not exhibit the above-mentioned disadvantages, which compositions contain, as the active ingredient, a compound of the general formula

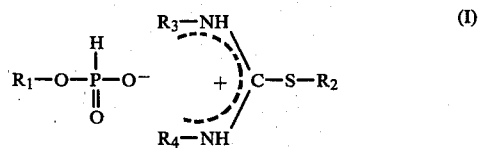

in which: $R_1$ is hydrogen or an alkyl radical containing from 1 to 6 carbon atoms, $R_2$ is an alkyl radical containing from 1 to 18 carbon atoms, $R_1$ and $R_2$ together may also represent an ethylene or propylene chain which is optionally substituted by alkyls containing from 1 to 3 carbon atoms, and $R_3$ and $R_4$, which are identical or different, are hydrogen or an alkyl radical containing from 1 to 18 carbon atoms, a cycloalkyl radical containing from 3 to 7 carbon atoms, an alkenyl radical containing from 3 to 18 carbon atoms, a phenyl radical or a benzyl radical, in association with an inert carrier which is acceptable in agriculture.

DESCRIPTION OF THE INVENTION

Some of these compounds are in themselves known and are described, in particular, by Orlovskii and Vovsi, Chemical Abstracts 70062m, volume 71, and J. B. Parker et al., Chemical Abstracts 12292h, volume 55, however only the preparation of these compounds is described, without mention of any existing or possible application thereof.

These compounds can be prepared in a manner which is in itself known; in the case of the compounds in which $R_1$ and $R_2$ have at most 6 carbon atoms, a symmetric or asymmetric dialkyl phosphite or a 1,3,2-dioxaphospholane or -phosphorinane is reacted with thiourea or a thiourea which is N-mono-substituted or N,N'-disubstituted by one or two alkyl radicals, in accordance with the equation:

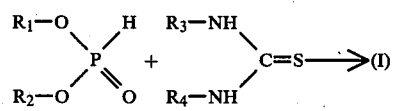

S-methylisothiouronium methyl-phosphite (compound 1) has been prepared in this way.

A mixture of thiourea (0.1 mol) and dimethyl phosphite (in excess) (40 ml) is heated to 130°–140° C. The rise in temperature is carefully controlled because the reaction is exothermic and starts suddenly. The reaction medium is kept at 130°–140° C. for 1 hour and then cooled. At 50° C., the isothiouronium salt precipitates. The medium is then diluted with acetone (200 ml). The precipitate is then filtered off, washed with acetone and then dried. A solid, which has a m.p. of 114° C. and of which analysis by nuclear magnetic resonance confirms the formula:

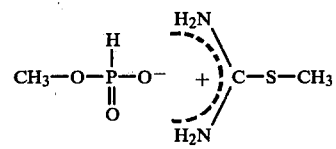

is thus obtained with a yield of 81%.

|  | Percentage analysis | | | |
| --- | --- | --- | --- | --- |
|  | C % | H % | N % | P % |
| Calculated | 19.36 | 5.96 | 15.05 | 16.64 |
| Found | 19.53 | 5.96 | 15.31 | 16.65 |

By following the above procedure with other symmetric or asymmetric dialkyl phosphites, the compounds 2 to 7, the yields and physical characteristics of which are mentioned in the following table, are obtained. For the compounds 8 to 10, a symmetric dialkyl phosphite is reacted with a N-monosubstituted or N,N'-disubstituted thiourea in acetonitrile solution, the medium being kept under reflux for 16 to 30 hours. The acetonitrile is then removed by distillation and the product is recovered in the form of a viscous oil.

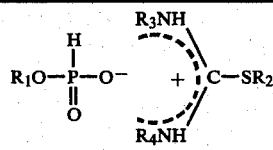

| Product No. | $R_1$ | $R_2$ | $R_3$ | $R_4$ | Yield | Physical constants | | C % | H % | N % | P % |
|---|---|---|---|---|---|---|---|---|---|---|---|
| 2 | $C_2H_5$ | $C_2H_5$ | H | H | 70% | M.p. = 107° C. | calc.: found: | 28.03 28.40 | 7.06 7.10 | 13.08 13.10 | 14.46 14.21 |
| 3 | iso-$C_3H_7$ | iso-$C_3H_7$ | H | H | 35% | M.p. = 165° C. | calc.: found: | 34.70 34.89 | 7.91 8.00 | 11.56 11.72 | 12.78 12.52 |
| 4 | n-$C_4H_9$ | n-$C_4H_9$ | H | H | 40% | M.p. = 110° C. | calc.: found: | 39.99 39.87 | 8.58 8.50 | 10.36 10.36 | 11.46 11.33 |
| 5 | n-$C_3H_7$ | n-$C_3H_7$ | H | H | 46% | M.p. = 95° C. | calc.: found: | 34.70 34.63 | 7.91 7.85 | 11.56 11.55 | 12.78 13.04 |
| 6 | sec-$C_4H_9$ | sec-$C_4H_9$ | H | H | 40% | M.p. = 155° C. | calc.: found: | 39.99 39.19 | 8.58 8.60 | 10.36 10.33 | 11.46 12.68 |
| 7 | iso-$C_3H_7$ | $CH_3$ | H | H | 50% | M.p. = 115° C. | calc.: found: | 28.03 27.78 | 7.06 7.09 | 13.08 13.07 | 14.46 13.86 |
| 8 | $CH_3$ | $CH_3$ | $CH_3$ | H | 100% | $n_D^{20}$: 1.527 | calc.: found: | 24.00 24.01 | 6.55 6.67 | 13.99 13.96 | |
| 9 | $CH_3$ | $CH_3$ | $CH_3$ | $CH_3$ | 100% | $n_D^{20}$: 1.503 | calc.: found: | 28.03 28.10 | 7.06 7.12 | 13.08 13.14 | 14.46 14.61 |
| 10 | $CH_3$ | $CH_3$ | $C_{12}H_{25}$ | H | 100% | M.p. = 35° C. | calc.: found: | 50.82 50.60 | 9.95 9.92 | 7.96 7.78 | 8.74 8.65 |

Preparation of internal isothiourea phosphites (compounds 11 and 12)

$$\left\{ \begin{array}{c} O \\ O \end{array} \right. \hspace{-2mm} \begin{array}{c} \diagdown \\ P \\ \diagup \end{array} \hspace{-2mm} \begin{array}{c} H \\ \diagdown \\ \diagup \\ O \end{array} + H_2N-\underset{\underset{S}{\|}}{C}-NH_2 \longrightarrow$$

$$-O-\underset{\underset{O}{\|}}{\overset{\overset{H}{|}}{P}}-O-CH_2-CH_2-CH_2-S-C\overset{\diagup NH_2}{\diagdown_{NH_2}} +$$

Molten 2-oxo-2H-1,3,2-dioxaphosphorinane (14.4 g) is heated to 120° C. At this temperature, thiourea (4.5 g) is added in small portions. The medium solidifies. It is cooled to ambient temperature and then dispersed in methanol (200 ml); the excess dioxaphosphorinane dissolves in the solvent, while the product remains dispersed therein. The precipitate is filtered off and dried.

A white solid (compound 11) (3 g., i.e. a yield of 25%), which melts at 180° C. is thus obtained.

| | Percentage analysis | | | |
|---|---|---|---|---|
| | C % | H % | N % | P % |
| Calculated | 24.24 | 5.59 | 14.14 | 15.63 |
| Found | 24.62 | 5.77 | 13.47 | 15.67 |

The lower homologue is obtained by following the same procedure, starting from 1,3,2-dioxaphospholane. The product (compound 12), obtained with a yield of 27%, has a m.p. of 182°-183° C.

Preparation of S-methylisothiouronium acid phosphite (compound 13)

by reaction of S-methylisothiourea, prepared in situ, with phosphorus acid.

S-Methylisothiouronium sulphate (13.9 g) is suspended in methanol (200 ml). Sodium methylate (0.1 mol) in solution in methanol (100 ml) is added. The mixture is allowed to react for 30 minutes, while stirring. The precipitate of sodium sulphate is filtered off and the S-methylisothiourea solution is neutralized with a solution of phosphorous acid (8.2 g) in methanol (100 ml). After concentration to dryness, the product crystallizes and it is recrystallized from 95% strength ethanol (80 ml). A solid, having a m.p. equal to 129° C., is obtained in a yield of 46.5%.

| | Percentage analysis | | | |
|---|---|---|---|---|
| | C % | H % | N % | P % |
| Calculated | 13.95 | 5.27 | 16.27 | 17.99 |
| Found | 14.30 | 5.29 | 16.03 | 17.87 |

The compounds of general Formula I may be prepared, according to another procedure, by dealkylation of symmetric or asymmetric dialkyl phosphites with isothiouronium halides in accordance with the equation:

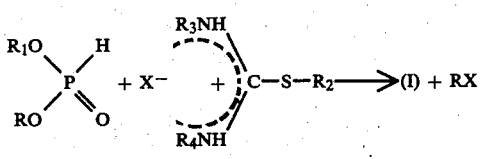

$R_1$ and $R_2$ being the same or different.

The reaction in principle is itself known; it has been described by V. V. Orlovski, B. A. Voski and V. E.

Mishkovich, J. Gen. Chem., USSR Vol. 42 p. 1924 (1972).

Using this procedure we have prepared S-alkylisothiouronium methyl- and ethyl-phosphites ($R_1$=Me or Et) by reacting dimethyl- or diethyl- phosphite with isothiouronium iodides.

S-Ethyl N-dodecylisothiouronium methyl-phosphite (compound 14) has been prepared in this way. A mixture of S-ethyl N-dodecylisothiouronium iodide (19 g; 0.035 mol) and dimethyl phosphite (4.4 g; 0.04 mol) is progressively heated. Methyl iodide starts to distill off towards 80° C. The mixture is kept for 15 minutes at 90° to 95° C. then cooled to 50° C. It is then dissolved in acetone (100 ml). The acetone solution is cooled using an acetone-solid carbon dioxide cooling bath; the product precipitates. The precipitate is filtered off, washed with cold acetone (20 ml), filtered off and dried in vacuo at ambient temperature. A white solid, melting at 38° C. is obtained in a yield of 82% (relative to the starting iodide) and its infrared spectrum confirms the formula:

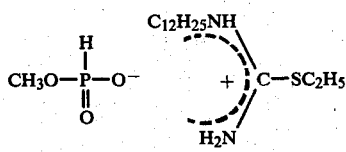

The elementary analysis is given in the table below.

By proceeding as described above with other isothiouronium iodides and other lower dialkyl phosphites, compounds 15 to 33, 36 and 38 to 57 were prepared. The yields (calculated relative to the iodide starting materials) and the characteristics of these compounds are given in the following tables.

This process is very suitable for the lower alkyl phosphites but it is more difficult to put into practice to prepare higher alkyl phosphites.

A variation of this process consists in reacting an asymmetric phosphite having a lower alkyl group (preferably a methyl group) and a higher alkyl group with an S-alkylisothiouronium halide in accordance with the equation:

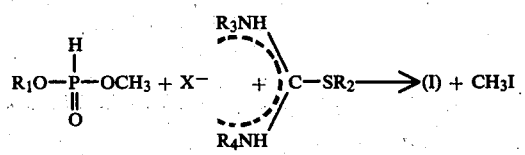

The reaction conditions are the same as those described in the preceding example.

The products, when they are solid, are isolated either by recrystallization from acetone or an apolar solvent such as hexane, cyclohexane or petroleum ether or, when the products are oily, by distillation under reduced pressure (about $10^{-2}$ mm. Hg.) of the excess dialkyl phosphite.

The S-alkylisothiouronium iodides were obtained in known manner by reaction of an alkyl iodide and a thiourea in accordance with the equation:

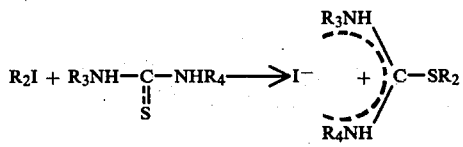

The following tables give, for each meaning of the radicals $R_1$ to $R_4$, the yield of the reaction to prepare the product, as well as the physical constants and the elementary analysis of the product obtained.

In addition, the formulae were verified by NMR and infrared spectra for the compounds having alkyl groups containing more than 6 carbon atoms.

In the following tables, "C" and "F" mean, respectively, "Calculated" and "Found".

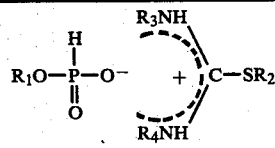

| Product No. | $R_1$ | $R_2$ | $R_3$ | $R_4$ | Yield | Physical constants | | C % | H % | N % | P % | S % |
|---|---|---|---|---|---|---|---|---|---|---|---|---|
| 14 | CH3 | C2H5 | C12H25 | H | 82% | M.p. = 38° C. | C: | 52.15 | 10.12 | 7.60 | 8.40 | 8.70 |
|  |  |  |  |  |  |  | F: | 52.00 | 9.94 | 7.68 | 8.60 | 8.76 |
| 15 | CH3 | CH3 | C16H33 | CH3 | 80% | M.p. = 35° C. | C: | 56.60 | 10.61 | 6.60 | 7.31 |  |
|  |  |  |  |  |  |  | F: | 54.44 | 10.63 | 5.96 | 7.27 |  |
| 16 | CH3 | CH3 | C14H29 | H | 92% | M.p. = 46° C. | C: | 53.40 | 10.20 | 7.32 | 8.11 |  |
|  |  |  |  |  |  |  | F: | 52.46 | 10.20 | 7.16 | 8.97 |  |
| 17 | CH3 | CH3 | C14H29 | CH3 | 30% | M.p. = 32° C. | C: | 54.54 | 10.35 | 7.07 | 7.82 |  |
|  |  |  |  |  |  |  | F: | 51.66 | 10.45 | 6.65 | 8.08 |  |
| 18 | CH3 | CH3 | ⟨O⟩- | H | 60% | M.p. = 121° C. | C: | 41.22 | 5.76 | 10.68 | 11.81 | 12.23 |
|  |  |  |  |  |  |  | F: | 41.30 | 5.75 | 10.51 | 11.68 | 12.35 |
| 19 | CH3 | CH3 | C12H25 | C12H25 | 77% | M.p. = 35° C. | C: | 62.03 | 11.37 | 5.36 | 5.92 | 6.13 |
|  |  |  |  |  |  |  | F: | 61.67 | 11.35 | 5.21 | 6.05 | 6.32 |
| 20 | CH3 | CH3 | C18H37 | CH3 | 94% | M.p. = 47° C. | C: | 58.37 | 10.91 | 6.19 | 6.84 | 7.68 |
|  |  |  |  |  |  |  | F: | 57.05 | 9.40 | 6.19 | 6.88 | 7.14 |
| 21 | CH3 | CH3 | ⟨O⟩-CH2- | ⟨O⟩-CH2- | 100% | $n_D^{20}$: 1.575 | C: | 55.73 | 6.33 | 7.65 | 8.45 | 8.75 |
|  |  |  |  |  |  |  | F: | 52.78 | 6.35 | 7.16 | 9.66 | 8.32 |

-continued

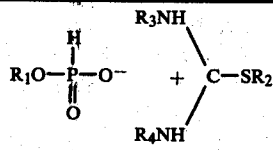

| Product No. | R₁ | R₂ | R₃ | R₄ | Yield | Physical constants | | C % | H % | N % | P % | S % |
|---|---|---|---|---|---|---|---|---|---|---|---|---|
| 22 | $CH_3$ | $CH_3$ | $C_{12}H_{25}$ | $CH_3$ | 100% | $n_D^{20}$: 1.490 | C: | 52.15 | 10.12 | 7.60 | 8.40 | 8.70 |
|  |  |  |  |  |  |  | F: | 51.30 | 9.57 | 7.06 | 9.10 | 9.00 |
| 23 | $CH_3$ | $CH_3$ | $C_8H_{17}$ | $CH_3$ | 100% | $n_D^{20}$: 1.493 | C: | 46.14 | 9.36 | 8.97 | 9.91 | 10.26 |
|  |  |  |  |  |  |  | F: | 46.80 | 9.40 | 8.60 | 12.10 | 10.40 |
| 24 | $CH_3$ | $CH_3$ | $C_8H_{17}$ | H | 100% | $n_D^{20}$: 1.494 | C: | 44.28 | 9.12 | 9.39 | 10.38 | 10.75 |
|  |  |  |  |  |  |  | F: | 42.42 | 9.10 | 8.50 | 11.85 | 10.82 |
| 25 | $CH_3$ | $CH_3$ | $\begin{array}{c}CH=CH_2\\|\\CH_2\\|\end{array}$ | H | 100% | $n_D^{20}$: 1.531 | C: | 31.85 | 6.68 | 12.38 | 13.69 | 14.17 |
|  |  |  |  |  |  |  | F: | 30.70 | 6.73 | 11.94 | 13.14 | 14.65 |
| 26 | $CH_3$ | $CH_3$ | $C_{10}H_{21}$ | H | 100% | $n_D^{20}$: 1.492 | C: | 47.85 | 9.50 | 8.58 | 9.50 |  |
|  |  |  |  |  |  |  | F: | 46.38 | 9.50 | 8.36 | 10.36 |  |
| 27 | $CH_3$ | $CH_3$ | $C_{10}H_{21}$ | $CH_3$ | 100% | $n_D^{20}$: 1.491 | C: | 49.41 | 9.70 | 8.23 | 9.11 |  |
|  |  |  |  |  |  |  | F: | 49.09 | 9.57 | 7.85 | 9.91 |  |
| 28 | $C_2H_5$ | $CH_3$ | $C_{12}H_{25}$ | H | 38% | M.p. = 40° C. | C: | 52.15 | 10.12 | 7.60 | 8.40 | 8.70 |
|  |  |  |  |  |  |  | F: | 51.45 | 9.85 | 7.55 | 7.92 | 8.53 |
| 29 | $CH_3$ | $CH_3$ | $C_6H_{13}$ | H | 85% | honey | C: | 40 | 8.52 | 10.37 | 11.47 |  |
|  |  |  |  |  |  |  | F: | 38.8 | 8.52 | 10.01 | 12.3 |  |
| 30 | $CH_3$ | $CH_3$ | $C_6H_{13}$ | $CH_3$ | 100% | honey | C: | 42.25 | 8.80 | 9.86 | 10.90 |  |
|  |  |  |  |  |  |  | F: | 40.9 | 8.67 | 9.62 | 10.27 |  |
| 31 | $CH_3$ | $CH_3$ | ⟨H⟩ | H | 78% | M.p. = 116.5° C. | C: | 40.30 | 7.84 | 10.45 | 11.56 |  |
|  |  |  |  |  |  |  | F: | 40.10 | 7.84 | 10.25 | 11.65 |  |
| 32 | $CH_3$ | $CH_3$ | ⟨H⟩ | $CH_3$ | 100% | honey | C: | 42.86 | 8.21 | 10.00 | 11.06 |  |
|  |  |  |  |  |  |  | F: | 42.20 | 8.31 | 9.28 | 10.88 |  |
| 33 | $CH_3$ | $CH_3$ | ⟨○⟩—$CH_2$ | H | 100% | $n_D^{20}$ 1.566 | C: | 43.47 | 6.20 | 10.14 | 11.21 | 11.60 |
|  |  |  |  |  |  |  | F: | 42.18 | 6.25 | 9.48 | 10.96 | 11.20 |
| 34 | $CH_3$ | $C_{12}H_{25}$ | H | H | 76% | M.p. = 122° C. | C: | 49.39 | 9.77 | 8.23 | 9.10 | 9.42 |
|  |  |  |  |  |  |  | F: | 49.47 | 9.64 | 8.09 | 9.70 | 10.16 |
| 35 | $CH_3$ | $C_{12}H_{25}$ | $CH_3$ | H | 73% | M.p. = 53° C. | C: | 50.82 | 9.95 | 7.90 | 8.74 | 9.04 |
|  |  |  |  |  |  |  | F: | 50.44 | 9.80 | 7.76 | 8.61 | 10.12 |
| 36 | $CH_3$ | $CH_3$ | $C_{18}H_{37}$ | H | 82% | M.p. = 41° C. | C: | 57.50 | 10.80 | 6.39 | 7.06 | 7.31 |
|  |  |  |  |  |  |  | F: | 57.95 | 11.03 | 5.82 | 7.20 | 7.28 |
| 37 | $CH_3$ | $C_{12}H_{25}$ | $C_{12}H_{25}$ | H | 90% | M.p. = 26° C. | C: | 61.62 | 10.94 | 5.53 | 6.11 | 6.33 |
|  |  |  |  |  |  |  | F: | 60.00 | 11.17 | 5.44 | 6.90 | 5.47 |
| 38 | $CH_3$ | $CH_3$ | $C_{16}H_{33}$ | H | 93% | M.p. = 48° C. | C: | 55.6 | 10.48 | 6.82 | 7.56 |  |
|  |  |  |  |  |  |  | F: | 54.33 | 10.44 | 6.36 | 8.48 |  |
| 39 | $CH_3$ | $CH_3$ | $C_{13}H_{27}$ | H | 70% | M.p. = 49° C. | C: | 52.15 | 10.12 | 7.60 | 8.40 |  |
|  |  |  |  |  |  |  | F: | 51.89 | 10.05 | 7.62 | 8.77 |  |
| 40 | $CH_3$ | $CH_3$ | ⟨H⟩ | ⟨H⟩ | 92% | M.p. = 144° C. | C: | 51.43 | 8.86 | 8.00 | 8.85 |  |
|  |  |  |  |  |  |  | F: | 51.23 | 8.95 | 7.86 | 9.07 |  |
| 41 | $CH_3$ | $CH_3$ | $C_6H_{13}$ | $C_6H_{13}$ | 88% | $n_D^{22}$: 1.488 | C: | 50.8 | 9.88 | 7.9 | 8.8 |  |
|  |  |  |  |  |  |  | F: | 49.34 | 9.41 | 7.47 | 9.15 |  |
| 42 | $CH_3$ | $CH_3$ | $C_{15}H_{31}$ | H | 80% | M.p. = 57.5° C. | C: | 54.54 | 10.35 | 7.07 | 7.82 |  |
|  |  |  |  |  |  |  | F: | 54.10 | 10.40 | 7.01 | 7.73 |  |
| 43 | $CH_3$ | $CH_3$ | $C_{15}H_{31}$ | $CH_3$ | 40% | M.p. = 39° C. | C: | 55.6 | 10.5 | 6.8 | 7.5 |  |
|  |  |  |  |  |  |  | F: | 54.22 | 10.6 | 6.98 | 7.55 |  |
| 44 | $CH_3$ | $CH_3$ | $C_8H_{17}-CH=$ $=CH-(CH_2)_8-$ | H | 57% | M.p. = 30° C. | C: | 54.54 | 10.35 | 7.07 | 7.82 |  |
|  |  |  |  |  |  |  | F: | 54.40 | 10.40 | 7.00 | 7.73 |  |
| 45 | $CH_3$ | $CH_3$ | $C_{11}H_{23}$ | H | 94% | M.p. = 38° C. | C: | 49.41 | 9.71 | 8.24 | 9.12 |  |
|  |  |  |  |  |  |  | F: | 48.41 | 9.74 | 7.95 | 8.49 |  |
| 46 | iso $C_3H_7$ | $CH_3$ | $C_{12}H_{25}$ | H | 89% | M.p. = 68° C. | C: | 53.33 | 10.20 | 7.32 | 8.10 | 8.37 |
|  |  |  |  |  |  |  | F: | 51.95 | 10.12 | 7.05 | 8.27 | 8.32 |
| 47 | iso $C_3H_7$ | $CH_3$ | $C_{16}H_{33}$ | H | 95% | M.p. = 52.5° C. | C: | 57.53 | 10.73 | 6.39 | 7.08 |  |
|  |  |  |  |  |  |  | F: | 56.53 | 10.71 | 6.18 | 6.84 |  |
| 48 | iso $C_3H_7$ | $CH_3$ | $C_{14}H_{29}$ | H | 95% | M.p. = 50.5° C. | C: | 55.61 | 10.49 | 6.83 | 7.56 |  |
|  |  |  |  |  |  |  | F: | 54.47 | 10.48 | 6.58 | 7.59 |  |
| 49 | $C_2H_5$ | $CH_3$ | $C_{16}H_{33}$ | H | 96% | pasty solid | C: | 56.60 | 10.61 | 6.60 | 7.31 |  |
|  |  |  |  |  |  |  | F: | 53.69 | 10.41 | 6.03 | 8.62 |  |

-continued

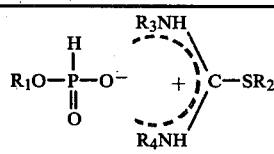

| Product No. | $R_1$ | $R_2$ | $R_3$ | $R_4$ | Yield | Physical constants | | C % | H % | N % | P % | S % |
|---|---|---|---|---|---|---|---|---|---|---|---|---|
| 50 | $C_2H_5$ | $CH_3$ | $C_{14}H_{29}$ | H | 76% | M.p. = 52.6° C. | C: | 54.55 | 10.35 | 7.07 | 7.93 | |
| | | | | | | | F: | 53.92 | 10.37 | 6.92 | 8.24 | |
| 51 | $CH_3$ | $C_2H_5$ | $C_{13}H_{27}$ | H | 100% | M.p. = 37° C. | C: | 53.38 | 10.28 | 7.32 | 8.10 | 8.38 |
| | | | | | | | F: | 51.8 | 10 | 7.10 | 8.9 | 8.26 |
| 52 | $CH_3$ | iso $C_3H_7$ | $C_{12}H_{25}$ | H | | M.p. = 35° C. | C: | 53.38 | 10.28 | 7.32 | 8.10 | 8.38 |
| | | | | | | | F: | 51.89 | 10.12 | 7.04 | 8.36 | 8.36 |
| 53 | $CH_3$ | $C_2H_5$ | n $C_6H_{13}$ | n $C_6H_{13}$ | 100% | $n_D^{20} = 1.490$ | C: | 52.15 | 10.12 | 7.60 | 8.40 | 8.70 |
| | | | | | | | F: | 50.38 | 9.88 | 7.20 | 8.70 | 9.00 |
| 54 | $CH_3$ | $CH_3$ | n $C_4H_9$ | n $C_4H_9$ | 96% | $n_D^{20} = 1.502$ | C: | 44.28 | 9.12 | 9.39 | 10.38 | 10.75 |
| | | | | | | | F: | 43.18 | 8.80 | 9.05 | 10.2 | 10.95 |
| 55 | $CH_3$ | $CH_3$ | n-$C_5H_{11}$ | n $C_5H_{11}$ | 98% | $n_D^{20} = 1.496$ | C: | 47.85 | 9.50 | 8.58 | 9.50 | 9.80 |
| | | | | | | | F: | 46.04 | 8.87 | 8.15 | 10.21 | 9.35 |
| 56 | $CH_3$ | $CH_3$ | n $C_7H_{15}$ | n $C_7H_{15}$ | 97% | $n_D^{20} = 1.488$ | C: | 53.40 | 10.20 | 7.32 | 8.11 | 8.4 |
| | | | | | | | F: | 51.43 | 9.91 | 7.09 | 8.37 | 8.15 |
| 57 | $CH_3$ | $CH_3$ | n $C_8H_{17}$ | n $C_8H_{17}$ | 97% | $n_D^{20} = 1.487$ | C: | 55.6 | 10.48 | 6.82 | 7.56 | 8.48 |
| | | | | | | | F: | 54.45 | 10.16 | 6.84 | 8.10 | 7.94 |
| 58 | $CH_3$ | $CH_3$ | n-$C_9H_{19}$ | n-$C_9H_{19}$ | 96% | $n_D^{20} = 1.483$ | C: | 57.50 | 10.80 | 6.39 | 7.06 | 7.31 |
| | | | | | | | F: | 56.61 | 10.62 | 6.20 | 7.98 | 7.65 |
| 59 | $CH_3$ | $CH_3$ | iso-$C_9H_{19}$ | iso-$C_9H_{19}$ | 96% | $n_D^{20} = 1.490$ | C: | 57.50 | 10.80 | 6.39 | 7.06 | 7.31 |
| | | | | | | | F: | 55.94 | 10.57 | 6.38 | 7.35 | 7.86 |
| 60 | $CH_3$ | n-$C_4H_{19}$ | n $C_6H_{13}$ | n $C_6H_{13}$ | 100% | $n_D^{20} = 1.489$ | C: | 54.52 | 10.42 | 7.06 | 7.81 | 8.09 |
| | | | | | | | F: | 52.88 | 10.15 | 7.25 | 7.86 | 8.42 |
| 61 | $CH_3$ | $CH_3$ | $C_{12}H_{25}$ | n-$C_6H_{13}$ | 100% | $n_D^{20} = 1.4845$ | C: | 57.50 | 10.80 | 6.39 | 7.06 | 7.32 |
| | | | | | | | F: | 56.84 | 10.69 | 6.34 | 8.2 | 7.10 |

The fungicidal products containing the compounds according to the invention are illustrated in the following examples:

Example 1a: in vivo test against Plasmopara viticola on vine plants (preventive treatment)

Vine plants (Gamay variety), cultivated in pots, are treated by spraying the underside of the leaves, using a gun, with an aqueous suspension of a wettable powder having the following composition by weight:

| | |
|---|---|
| active ingredient to be tested | 20% |
| deflocculant (calcium lignosulphate) | 5% |
| wetting agent (sodium alkylarylsulphonate) | 1% |
| filler (aluminum silicate) | 74% | at the desired dilution, which contains at the relevant dose, the active ingredient to be tested; each test is repeated three times.

After 48 hours, contamination is carried out by spraying the underside of the leaves with an aqueous suspension of fungus spores (about 80,000 units/cc.). The pots are then placed for 48 hours in an incubation cell at 100% relative humidity and at 20° C.

The plants are checked 9 days after infestation.

Under these conditions, it is observed that, at a dose of 0.5 g./liter, the compounds, 1,2,5,10,11,14,16,24,31,34,35,36,37,38,39,41,42,43,44 to 50,53,55 and 59 effect a total protection (>95%) and the compounds 6,13,18 and 33 effect a good protection (from 75 to 95%).

Example 1b: in vivo systemic test against vine mildew by absorption through the roots Several vine plants (Gamay variety), each of which is in a pot containing a nutrient solution, are watered with an aqueous solution (100 cc.) containing the ingredient to be tested (0.5 g./liter). After five days, the vine is contaminated with an aqueous suspension containing Plasmopara viticola (100,000 spores/cc.). Incubation is allowed to proceed for 48 hours in a chamber at 20° C. and at 100% relative humidity. The degree of infestation is observed after about 9 days by comparison with an infested control plant which has been watered with distilled water (40 cc.).

Under these conditions, it is observed that compounds 1,2 and 5, absorbed by the roots, effect a total protection of the vine leaves against the mildew, which clearly shows the systemic character of these compounds.

Example 3: In vivo survival test against Phytophthora infestans on tomato leaves Tomato leaves (Marmande variety), which have been cultivated in a greenhouse and are 60 to 75 days old, are treated by spraying them with a suspension (containing 2 g./liter of active ingredient) of the product to be tested.

After 48 hours, the leaves are cut off and placed in Petri dishes (diameter: 11 cm.), the bottom of which has been covered with a moist filter paper beforehand (5 folioles/dish; 2 dishes/product/dose). The inoculum is then applied by depositing plugs of filter paper (diameter: 9 mm.) soaked with a suspension of spores (3 plugs/foliole). The suspension of spores (zoo sporangia) is obtained from a Phytophthora infestans culture on a medium based on flour of 20 day old chick-peas.

The experiment is kept at 16° C. for 8 days.

Observations are made by evaluating the surface area infested by the fungus. Under these conditions, it is observed that the compound No. 10 effects a total protection of the tomato leaves against the mildew.

Example 4: In vivo test against *Uromyces phaseoli* responsible for bean blight Bean plants are cultivated in pots 8 cm. in diameter. At the two cotyledonous leaf stage the plants are treated by spraying with the product to be tested at the desired dose. After 48 hours the beans are sprayed with a suspension of spores (50,000 sp./cm.$^3$) obtained from contaminated plants. The beans are then placed in a climatic cell regulated in the following manner:

| Lighting | 16 hours |
|---|---|
| Day temperature | 20° C. |
| Night temperature | 15° C. |
| Relative humidity | 100% | for 48 hours then the humidity is reduced to 80%.

Inspection is carried out on the 15th day after contamination, by comparison with an untreated control.

Under these conditions it is observed that at the dose of 0.5 g./l., the compounds 10, 14, 16, 19, 26, 35, 37, 38, 39, 41, 42, 43, 44 to 50, 53 and 55 to 59 effect a superior protection in 75% of the bean plants.

Example 5: in vitro test on fungistatic action

The action of the compounds of the invention on the development of the following fungi is studied.

*Piricularia oryzae*, responsible for piriculariosis in rice;
*Pseudomonas phaseolicola* responsible for a bacterial illness.

Each experiment is carried out in the following manner: 5 ml. portions of gelose (malt/agar medium) are placed in test tubes and each tube is then stoppered and sterilized for 20 minutes at 120° C. The tubes are then placed in a water-bath kept at 60° C.

A predetermined amount of a 1% solution of the compounds to be tested in acetone is then injected, by means of a pipette, into each tube, in order to obtain in the gelose culture medium a predetermined concentration of the compound to be tested.

At the end of 24 hours, the tubes are inoculated either by injection using a syringe, of 0.5 ml. of a spore suspension containing about 100,000 sp./ml. or by a streak of bacterial culture. As a control, a tube is taken which is similar to that described above, but in which the gelose medium does not contain any active material.

After one week in the case of the piriculariosis or 24 hours in the case of *Pseudomonas phaseolicola*, at 26° C., in dark, the growth of the microorganism is evaluated for a given concentration of active material, and compared, in the aggregate, with that of an untreated control and expressed on a scale of 0 to 4, 0 corresponding to a growth identical to that of the control and 4 corresponding to complete inhibition of the development of the microorganism.

Under these conditions it is observed that: at a dose of 0.2 g./l. compounds 41 and 56 to 60 effect a total inhibition (>95%) and compounds 14, 38 and 53 a good inhibition (75 to 95%) of *Piricularia oryzae*, and that the compounds 14, 22, 24, 26, 27, 39, 41, 42, 43, 45, 53, 54 to 61 effect a total inhibition of the bacterium *Pseudomonas phaseolicola*.

The above examples clearly illustrate the remarkable fungicidal properties (activity and systemic behavior) of the compounds according to the invention, especially against phycomycetes, and also their lack of phytotoxicity. These compounds can therefore be used for combatting fungal diseases, in both a preventive and a curative capacity, and especially for combatting those diseases due to phycomycetes, basidiomycetes, Ascomycetes and Fungi Imperfecti, and in particular the various forms of mildew, in plants in general and, in particular, in vine, tobacco, hop and tomato plants, cereals and cucurbitaceae.

The use doses can vary within wide limits, depending on the virulence of the fungus and on the climatic conditions.

In general, compositions containing from 0.1 to 5 g./liter of active ingredient are very suitable.

For their use in practice, the compounds according to the invention form part of compositions which generally comprise, in addition to the active ingredient according to the invention, a carrier and/or a surface-active agent.

The term "carrier", for the purpose of the present description, denotes an organic or inorganic, natural or synthetic material with which the active ingredient is combined in order to facilitate its application to the plant, to seeds or to the soil, or in order to facilitate its transportation or handling. This carrier must therefore be inert and acceptable in agriculture, especially to the plant. The carrier can be solid (clays, natural or synthetic silicates, resins, waxes, solid fertilizers or the like) or liquid (water, alcohols, ketones, a petroleum fraction, chlorohydrocarbons or liquified gases).

The surface-active agent can be an emulsifier, dispersing agent or wetting agent, which can be ionic or non-ionic. Examples which may be mentioned are salts of polyacrylic acids and of ligninsulphonic acids, and products resulting from the condensation of ethylene oxide with fatty alcohols, fatty acids or fatty amines. The presence of at least one surface-active agent is essential when the inert carrier is a liquid.

The compositions according to the invention can be prepared in the form of wettable powders, soluble powders, dusting powders, granules, solutions, in particular aqueous solutions, emulsifiable concentrates, emulsions, suspension concentrates and aerosols.

The wettable powders are usually prepared so that they contain from 20 to 95% by weight of active ingredient, and they usually contain, in addition to a solid carrier, from 0 to 5% by weight of a wetting agent, from 3 to 10% by weight of a dispersing agent and, where necessary, from 0 to 10% by weight of one or more stabilizers and/or other additives such as penetrating agents, adhesives and anti-caking agents, dyestuffs and the like.

By way of example, the composition of a wettable powder is given:

| active ingredient (compound no. 1) | 50% |
|---|---|
| calcium lignosulphate (deflocculant) | 5% |
| anionic wetting agent (alkylarylsulphonate) | 1% |
| anti-caking silica | 5% |
| kaolin (filler) | 39% |

The water-soluble powders are obtained in the customary manner by mixing from 20 to 95% by weight of the active ingredient with from 0 to 10% of an anti-caking filler, the remainder consisting of a water-soluble solid carrier, especially a salt.

An example of the composition of a soluble powder is given:

| | |
|---|---|
| active ingredient (compound no. 2) | 70% |
| anionic wetting agent | 0.5% |
| anti-caking silica | 5% |
| sodium sulphate (solid carrier) | 24.5% |

The emulsion concentrates which can be applied by spraying, after dilution in water, usually contain the active ingredient in solution in a solvent and, in addition to the solvent and, where necessary, a co-solvent, from 10 to 50% by weight/volume of active ingredient and from 2 to 20% by weight/volume of suitable additives such as stabilizers, penetrating agents, corrosion inhibitors and dyestuffs and adhesives.

By way of example, the composition of an emulsifiable concentrate is given, the amounts being expressed in g./liter:

| | |
|---|---|
| active ingredient (compound no. 4) | 125 g./liter |
| sodium dodecylbenzenesulphonate | 24 g./liter |
| nonylphenol oxyethyleneated with 10 molecules of ethylene oxide | 16 g./liter |
| cyclohexanone | 200 g./liter |
| aromatic solvent | q.s.p. l/liter |

The suspension concentrates, which can also be applied by spraying, are prepared so as to give a stable fluid product which does not form a deposit, and they usually contain from 10 to 75% by weight of active ingredient, from 0.5 to 15% by weight of surface-active agents, from 0.1 to 10% by weight of anti-sedimentation agents, such as protective colloids and thixotropic agents, from 0 to 10% by weight of suitable additives, such as anti-foam agents, corrosion inhibitors, stabilizers, penetrating agents and adhesives, and, as the carrier, water or an organic liquid in which the active ingredient is essentially insoluble; certain organic solid materials or inorganic salts can be dissolved in the carrier to assist in preventing sedimentation or to act as anti-freeze agents for the water.

Aqueous dispersions and aqueous emulsions, e.g. compositions obtained by diluting, with water, a wettable powder or an emulsifiable concentrate according to the invention, at a rate of 10 to 100 g. of active ingredient per hectoliter of water, fall within the general scope of the present invention. These emulsions can be of the water-in-oil type or of the oil-in-water type and they can have a thick consistency such as that of a "mayonnaise".

The compositions according to the invention can contain other ingredients, e.g. protective colloids, adhesives or thickeners, thixotropic agents, stabilizers or sequestering agents, as well as other known active ingredients having pesticidal properties, in particular insecticidal or fungicidal properties.

What is claimed is:

1. A fungicidal and bactericidal composition for combatting fungal and bacterial diseases in plants, which contains an effective amount of a compound of the formula:

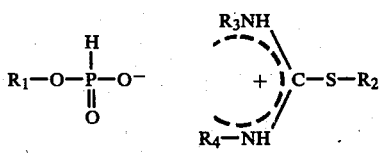

in which
R₁ is hydrogen or an alkyl radical containing from 1 to 6 carbon atoms,
R₂ is an alkyl radical containing from 1 to 18 carbon atoms, R₁ and R₂ can additionally form an ethylene or propylene chain which is optionally substituted by alkyls containing from 1 to 3 carbon atoms, and
R₃ and R₄, which are identical or different, are hydrogen, an alkyl radical containing from 1 to 18 carbon atoms, a cycloalkyl radical containing from 3 to 7 carbon atoms, an alkenyl radical containing from 3 to 18 carbon atoms, the phenyl radical or the benzyl radical, in association with an inert solid carrier which is acceptable in agriculture.

2. A fungicidal composition for combatting fungal diseases in plants, which contains a fungicidally effective amount of a compound of the formula:

$$R_1-O-\underset{\underset{O}{\|}}{\overset{\overset{H}{|}}{P}}-O^- \quad + \quad \begin{matrix} R_3NH \\ \diagdown \\ C-S-R_2 \\ \diagup \\ R_4-NH \end{matrix}$$

in which:
R₁ is hydrogen or an alkyl radical containing from 1 to 6 carbon atoms,
R₂ is an alkyl radical containing from 1 to 6 carbon atoms, R₁ and R₂ can additionally form an ethylene or propylene chain which is optionally substituted by alkyls containing from 1 to 3 carbon atoms, and
R₃ and R₄, which are identical or different, are hydrogen or an alkyl radical containing from 1 to 18 carbon atoms, in association with an inert solid carrier which is acceptable in agriculture.

3. A fungicidal composition according to claim 2, in which, in the formula of the active ingredient, R₃ and R₄ are hydrogen.

4. A fungicidal composition according to claim 2, which contains, as the active ingredient, a compound for the formula:

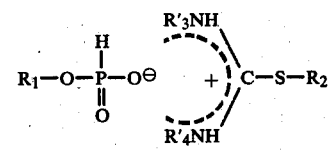

in which:
R₁ and R₂ have the same meaning as in claim 2 and R'₃ and R'₄ represent hydrogen or an alkyl radical containing from 6 to 18 carbon atoms, with the proviso that only one of the radicals R'₃ an R'₄ is a hydrogen atom.

5. A fungicidal composition according to claim 4, in which the active ingredient is S-methyl N-dodecyisothiouronium methyl-phosphite.

6. A fungicidal composition according to claim 4, in which the active ingredient is S-ethyl N-dodecyisothiouronium methyl-phosphite.

7. A fungicidal composition according to claim 4, in which the active ingredient is S-methyl N,N'-di-n-hexylisothiouronium methyl-phosphite.

8. A fungicidal and bactericidal composition for combatting fungal and bacterial diseases in plants, which contains an effective amount of a compound of the formula:

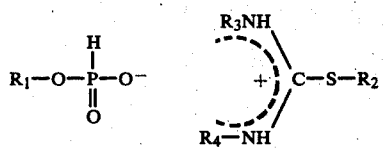

in which $R_1$ is hydrogen or an alkyl radical containing from 1 to 6 carbon atoms, $R_2$ is an alkyl radical containing from 1 to 18 carbon atoms, $R_1$ and $R_2$ can additionally form an ethylene or propylene chain which is optionally substituted by alkyls containing from 1 to 3 carbon atoms, and $R_3$ and $R_4$, which are identical or different, are hydrogen, an alkyl radical containing from 1 to 18 carbon atoms, a cycloalkyl radical containing from 3 to 7 carbon atoms, an alkenyl radical containing from 3 to 18 carbon atoms, the phenyl radical or the benzyl radical, in combination with an inert carrier and a surface-active agent, said carrier and said surface active agent being acceptable in agriculture.

9. A fungicidal composition according to claim 8, in which said inert carrier is a liquid.

10. A fungicidal composition for combatting fungal diseases in plants, which contains a fungicidally effective amount of a compound of the formula:

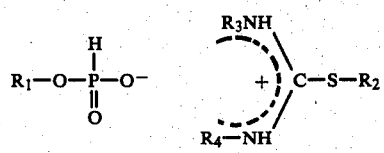

in which:

$R_1$ is hydrogen or an alkyl radical containing from 1 to 6 carbon atoms, $R_2$ is an alkyl radical containing from 1 to 6 carbon atoms, $R_1$ and $R_2$ can additionally form an ethylene or propylene chain which is optionally substituted by alkyls containing from 1 to 3 carbon atoms, and $R_3$ and $R_4$, which are identical or different, are hydrogen or an alkyl radical containing from 1 to 18 carbon atoms, in combination with an inert carrier and a surface-active agent, said carrier and said surface-active agent being acceptable in agriculture.

11. A fungicidal composition according to claim 10, in which, in the formula of the active ingredient, $R_3$ and $R_4$ are hydrogen.

12. A fungicidal composition according to claim 10, which contains, as the active ingredient, a compound of the formula:

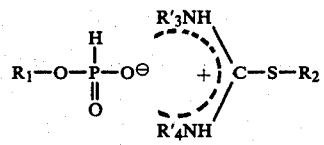

in which: $R_1$ and $R_2$ have the same meanings as in claim 10 and $R'_3$ and $R'_4$ represent hydrogen or an alkyl radical containing from 6 to 18 carbon atoms, with the proviso that only one of the radicals $R'_3$ and $R'_4$ may be a hydrogen atom.

13. A fungicidal composition according to claim 12, in which the active ingredient is S-methyl N-dodecyisothiouronium methyl-phosphite.

14. A fungicidal composition according to claim 12, in which the active ingredient is S-ethyl N-dodecylisothiouronium methyl-phosphite.

15. A fungicidal composition according to claim 12, in which the active ingredient is S-methyl N,N'-di-n-hexylisothiouronium methyl-phosphite.

16. A fungicidal composition according to claim 10, in which said carrier is a solid carrier.

17. A process for the protection or treatment of plants against fungal diseases, which comprises applying a fungicidally effective amount of a composition according to one of claims 1 to 7 or 8 to 16 to said plants, the environs thereof or the seeds thereof.

* * * * *